United States Patent
Muszynska

(10) Patent No.: US 6,524,610 B2
(45) Date of Patent: Feb. 25, 2003

(54) NUTRITIONAL COMPOSITION MADE FROM CONVENTIONAL FOODS FOR MIXING ONSITE IN A BLENDER AND TREATING PATIENTS WITH HEPATIC DISORDERS

(76) Inventor: Julia Muszynska, 108 Center St., Staten Island, NY (US) 10306

( * ) Notice: Subject to any disclaimer, the term of this patent is extended or adjusted under 35 U.S.C. 154(b) by 0 days.

(21) Appl. No.: 09/793,813

(22) Filed: Feb. 26, 2001

(65) Prior Publication Data

US 2002/0119181 A1 Aug. 29, 2002

(51) Int. Cl.$^7$ ................................................ A61K 47/00
(52) U.S. Cl. ...................... 424/439; 424/400; 514/893; 426/416; 426/443; 426/800
(58) Field of Search ................. 424/400, 439; 514/893

(56) References Cited

U.S. PATENT DOCUMENTS 6,102,706 A * 8/2000 Khoo et al. .................. 434/127

* cited by examiner

Primary Examiner—Thurman K. Page
Assistant Examiner—Charesse Evans

(57) ABSTRACT

A nutritional composition made from conventional food mixed on-site in a blender and treating patients with hepatic disorders. The composition includes a vitamin A enriched conventional food, a vitamin D enriched conventional food, a vitamin E enriched conventional food, a vitamin K enriched conventional food, a vitamin C enriched conventional food, a thiamine enriched conventional food, a riboflavin enriched conventional food, a niacin enriched conventional food; a pyridoxine enriched conventional food, a folic acid enriched conventional food, a pantothenic acid enriched conventional food, a vitamin B12 enriched conventional food, a biotin enriched conventional food, a choline enriched conventional food, a sodium enriched conventional food, a potassium enriched conventional food, a chlorine enriched conventional food, a calcium enriched conventional food, a phosphorus enriched conventional food, a magnesium enriched conventional food, a copper enriched conventional food, an Iodine enriched conventional food, a manganese enriched conventional food, and a zinc enriched conventional food.

20 Claims, 14 Drawing Sheets

| INGREDIENT | QUANTITY | INGREDIENT | QUANTITY |
|---|---|---|---|
| Protein (Nx 5.8) | 40.00 g | Vitamin B12 | 6.00 mcg |
| Carbohydrate | 290.00 g | Biotin | 300.00 mcg |
| Fat | 21.20 g | Choline | 400.00 mg |
| Minerals | 8.00 g | Taurine | 120.00 mg |
| Moisture | 761.60 g | L-Carnitine | 120.00 mg |
| Energy | 1500.00 Kcal 6280.00 KJ | Sodium | 320.00 mg |
| Vitamin A | 5000.00 IU 1500.00 mcg RE | Potassium | 1320.00 mg |
| Vitamin D | 400.00 IU 10.00 mcg | Chlorine | 1500.00 mg |
| Vitamin E | 30.00 IU | Calcium | 1000.00 mg |
| Vitamin K | 120.00 mcg | Phosphorus | 1000.00 mg |
| Vitamin C | 96.00 mg | Magnesium | 400.00 mg |
| Thiamine (B1) | 1.52 mg | Copper | 2.00 mg |
| Riboflavin (B2) | 1.72 mg | Iodine | 152.00 mcg |
| Niacin (PP) | 20.00 mg | Iron | 18.00 mg |
| Pyridoxine( B6) | 2.00 mg | Manganese | 4.00 mg |
| Folic Acid | 400.00 mcg | Zinc | 15.20 mg |
| Pantothenic Acid | 10.00 mg | - | - |

FIGURE 1

| INGREDIENT | QUANTITY | INGREDIENT | QUANTITY |
|---|---|---|---|
| Protein (Nx 5.8) | 40.00 g | Vitamin B12 | 6.00 mcg |
| Carbohydrate | 290.00 g | Biotin | 300.00 mcg |
| Fat | 21.20 g | Choline | 400.00 mg |
| Minerals | 8.00 g | Taurine | 120.00 mg |
| Moisture | 761.60 g | L-Carnitine | 120.00 mg |
| Energy | 1500.00 Kcal 6280.00 KJ | Sodium | 320.00 mg |
| Vitamin A | 5000.00 IU 1500.00 mcg RE | Potassium | 1320.00 mg |
| Vitamin D | 400.00 IU 10.00 mcg | Chlorine | 1500.00 mg |
| Vitamin E | 30.00 IU | Calcium | 1000.00 mg |
| Vitamin K | 120.00 mcg | Phosphorus | 1000.00 mg |
| Vitamin C | 96.00 mg | Magnesium | 400.00 mg |
| Thiamine (B1) | 1.52 mg | Copper | 2.00 mg |
| Riboflavin (B2) | 1.72 mg | Iodine | 152.00 mcg |
| Niacin (PP) | 20.00 mg | Iron | 18.00 mg |
| Pyridoxine (B6) | 2.00 mg | Manganese | 4.00 mg |
| Folic Acid | 400.00 mcg | Zinc | 15.20 mg |
| Pantothenic Acid | 10.00 mg | - | - |

FIGURE 2

| TYPE OF FAT | QUANTITY |
|---|---|
| Total fat | 21.2 gm |
| MCT | 13.76 gm |
| Canola Oil | 4.16 gm |
| Corn Oil | 1.12 gm |
| Milk Fat | 1.12 gm |
| Lecithin | 1.12 gm |
| Linoleic Acid | 1.58 gm |
| Vitamin E | 30 IU |
| Vitamin E: linoleic | 19 IU/gm |

FIGURE 3

| TYPE OF FAT | PERCENTAGE | PERCENTAGE OF ENERGY FROM FAT |
|---|---|---|
| MCT | 66% | 63% |
| Canola oil | 19% | 20% |
| Corn oil | 5% | 5.5% |
| Milk Fat | 5% | 5.5% |
| Lecithin | 5% | 6% |

FIGURE 4

| TYPE OF ACID | DESIGNATION | PERCENTAGE | QUANTITY |
|---|---|---|---|
| Butyric acid | ($C_{4:0}$) | 0.13% | .03 gm/liter |
| Caproic acid | ($C_{6:0}$) | 0.72% | 0.14 gm/liter |
| Caprylic acid | ($C_{8:0}$) | 38.36% | 7.42 gm/liter |
| Capric acid | ($C_{10:0}$) | 27.02% | 5.23 gm/liter |
| Lauric acid | ($C_{12:0}$) | 1.43% | 0.28 gm/liter |
| Myristic acid | ($C_{14:0}$) | 0.47% | 0.09 gm/liter |
| Palmitic acid | ($C_{16:0}$) | 2.80% | 0.54 gm/liter |
| Stearic acid | ($C_{18:0}$) | 1.16% | 0.22 gm/liter |
| Total | - | 72.09% | 13.95 gm/liter |

FIGURE 5

| TYPE OF ACID | DESIGNATION | PERCENTAGE | QUANTITY |
|---|---|---|---|
| Palmitoleic acid | ($C_{16:1}$) | 0.25% | 0.05 gm/liter |
| Oleic acid | ($C_{18:1}$) | 16.74% | 3.24 gm/liter |
| Linoleic acid | ($C_{18:2}$) | 8.38% | 1.62 gm/liter |
| Linolenic acid | ($C_{18:3}$) | 2.16% | 0.42 gm/liter |
| Erucic acid | ($C_{22:1}$) | 0.40% | 0.08 gm/liter |
| Total | | 27.93% | 5.41 gm/liter |

FIGURE 6

| AMINO ACID | 100 Kcal | 1500 Kcal | 250 ml | 100 ml |
|---|---|---|---|---|
| L-Leucine | 0.62 gm | 9.32 gm | 2.33 gm | 9.32 gm |
| L-Isoleucine | 0.51 gm | 7.72 gm | 1.93 gm | 7.72 gm |
| L-Valine | 0.41 gm | 6.20 gm | 1.55 gm | 6.20 gm |
| L-Lysine | 0.33 gm | 5.00 gm | 1.25 gm | 5.00 gm |
| L-Arginine | 0.32 gm | 4.80 gm | 1.20 gm | 4.80 gm |
| L-Proline | 0.17 gm | 2.48 gm | 0.62 gm | 2.48 gm |
| L-Glutamic acid | 0.14 gm | 2.08 gm | 0.52 gm | 2.08 gm |
| L-Alanine | 0.13 gm | 1.88 gm | 0.47 gm | 1.88 gm |
| L-Threonine | 0.10 gm | 1.52 gm | 0.38 gm | 1.52 gm |
| L-Histidine | 0.10 gm | 1.44 gm | 0.36 gm | 1.44 gm |
| L-Aspartic acid | 0.07 gm | 1.04 gm | 0.26 gm | 1.04 gm |
| Glycine | 0.05 gm | 0.76 gm | 0.19 gm | 0.76 gm |
| L-Serine | 0.04 gm | 0.64 gm | 0.16 gm | 0.64 gm |
| L-Methionine | 0.04 gm | 0.56 gm | 0.14 gm | 0.56 gm |
| L-Phenylalanine | 0.03 gm | 0.40 gm | 0.10 gm | 0.40 gm |
| L-Tyrosine | 0.02 gm | 0.32 gm | 0.08 gm | 0.32 gm |
| L-Tryptophane | 0.02 gm | 0.24 gm | 0.06 gm | 0.24 gm |
| L-Cystine | 0.01 gm | 0.16 gm | 0.04 gm | 0.16 gm |

FIGURE 7

| MINERAL | 100 Kcal | 1500 Kcal | 250 ml | 1000 ml |
|---|---|---|---|---|
| Sodium | 21.33 mg<br>0.93 mmol | 320.00 mg<br>13.92 mmol | 80.00 mg<br>3.48 mmol | 320.00 mg<br>13.92 mmol |
| Potassium | 88.00 mg<br>2.25 mmol | 1320.00 mg<br>33.76 mmol | 330.00 mg<br>8.44 mmol | 1320.00 mg<br>33.76 mmol |
| Chloride | 100.00 mg<br>2.82 mmol | 1500.00 mg<br>42.32 mmol | 375.00 mg<br>10.58 mmol | 1500.00 mg<br>42.32 mmol |
| Calcium | 66.67 mg<br>1.67 mmol | 1000.00 mg<br>25.00 mmol | 250.00 mg<br>6.25 mmol | 1000.00 mg<br>25.00 mmol |
| Phosphorus | 66.67 mg<br>2.15 mmol | 1000.00 mg<br>32.24 mmol | 250.00 mg<br>8.06 mmol | 1000.00 mg<br>32.24 mmol |
| Magnesium | 26.67 mg<br>1.10 mmol | 400.00 mg<br>16.44 mmol | 100.00 mg<br>4.11 mmol | 400.00 mg<br>16.44 mmol |
| Base excess | 0.36 mmol | 5.36 mmol | 1.34 mmol | 5.36 mmol |
| Renal solute | 21.20 mOsm | 318.00 mOsm | 29.50 mOsm | 318.00 mOsm |

FIGURE 8

| ELECTROLYTE | RATIO |
|---|---|
| Na/K | 3:0.4 |
| (Na + K)/Cl | 3:1.1 |
| Ca/P | 4:1.0 |

FIGURE 9

| PROTEIN SOURCE | PERCENTAGE |
|---|---|
| Free Amino Acid | 77% |
| Whey | 23% |

FIGURE 10

| Nitrogen to non-protein energy ratio (gm N/kcal) | 1:194 |
|---|---|
| Nitrogen to protein energy ratio (gm N/kcal) | 1:217 |

FIGURE 11

| INGREDIENT | CONVENTIONAL FOOD |
|---|---|
| Vitamin A | Fish Liver Oil, Liver, Carrots, Dark Green Vegetables, Dark Yellow Vegetables, Eggs, Milk Products, Dairy Products, Margarine, Yellow Fruits |

FIGURE 12

| INGREDIENT | CONVENTIONAL FOOD |
|---|---|
| Vitamin D | Fish Liver Oils, Sardines, Herring, Salmon, Tuna, Milk, Dairy Products |

FIGURE 13

| INGREDIENT | CONVENTIONAL FOOD |
|---|---|
| Vitamin E | Wheat Germ, Soybeans, Vegetable Oils, Nuts, Brussels Sprouts, Leafy Green Vegetables, Spinach, Enriched Flour, Whole Wheat, Whole-Grain Cereals, Eggs |

FIGURE 14

| INGREDIENT | CONVENTIONAL FOOD |
|---|---|
| Vitamin K | Leafy Green Vegetables, Yogurt, Alfalfa, Egg Yolk, Safflower Oil, Soybean Oil, Fish Liver Oils, Kelp |

FIGURE 15

| INGREDIENT | CONVENTIONAL FOOD |
|---|---|
| Vitamin C | Citrus Fruits, Berries, Green Vegetables, Leafy Vegetables, Tomatoes, Cauliflower, Potatoes, Peppers |

FIGURE 16

| INGREDIENT | CONVENTIONAL FOOD |
|---|---|
| Thiamine (B1) | Brewer's Yeast, Rick Husks, Unrefined Cereal Grains, Whole Wheat, Oatmeal, Peanuts, Organic Meats, Lean Pork, Vegetables, Bran, Milk |

FIGURE 17

| INGREDIENT | CONVENTIONAL FOOD |
|---|---|
| Riboflavin (B2) | Milk. Liver, Kidney, Yeast, Cheese, Leafy Green Vegetables, Fish, Eggs |

FIGURE 18

| INGREDIENT | CONVENTIONAL FOOD |
|---|---|
| Niacin (PP) | Liver, Lean Meat, Whole Wheat Products, Brewer's Yeast, Kidney, Wheat Germ, Fish, Eggs, Roasted Peanuts, Poultry White Meat, Avocados, Dates, Figs, Prunes |

FIGURE 19

| INGREDIENT | CONVENTIONAL FOOD |
|---|---|
| Pyridoxine (B6) | Brewer's Yeast, Wheat Bran, Wheat Germ, Liver, Kidney, Soy Beans, Cantaloupe, Cabbage, Blackstrap Molasses, Unmilled Rice, Eggs, Oats, Peanuts, Walnuts |

FIGURE 20

| INGREDIENT | CONVENTIONAL FOOD |
|---|---|
| Folic Acid | Deep-Green Leafy Vegetables, Carrots, Tortula Yeast, Liver, Egg Yolk, Cantaloupe, Apricots, Pumpkins, Avocados, Beans, Whole Rye Flour, Dark Rye Flour |

FIGURE 21

| INGREDIENT | CONVENTIONAL FOOD |
|---|---|
| Pantothenic Acid | Meat, Whole Grains, Wheat Germ, Bran, Kidney, Liver, Heart, Green Vegetables, Brewer's Yeast, Nuts, Chicken, Crude Molasses |

FIGURE 22

| INGREDIENT | CONVENTIONAL FOOD |
|---|---|
| Vitamin B12 | Liver, Beef, Pork, Eggs, Milk, Cheese, Kidney |

FIGURE 23

| INGREDIENT | CONVENTIONAL FOOD |
|---|---|
| Biotin | Beef Liver, Egg Yolk, Soy Flour, Brewer's Yeast, Milk, Kidney, Unpolished Rice |

FIGURE 24

| INGREDIENT | CONVENTIONAL FOOD |
|---|---|
| Choline | Egg Yolks, Brain, Heart, Green Leafy Vegetables, Yeast, Liver, Wheat Germ |

FIGURE 25

| INGREDIENT | CONVENTIONAL FOOD |
|---|---|
| Sodium | Salt, Shellfish, Carrots, Beets, Artichokes, Dried Beef, Brains, Kidney, Bacon |

FIGURE 26

| INGREDIENT | CONVENTIONAL FOOD |
|---|---|
| Potassium | Citrus Fruits, Cantaloupe, Tomatoes, Watercress, All Green Leafy Vegetables, Mint Leaves, sunflower Seeds, Bananas, Potatoes |

FIGURE 27

| INGREDIENT | CONVENTIONAL FOOD |
|---|---|
| Chlorine | Table Salt, Kelp, Olives |

FIGURE 28

| INGREDIENT | CONVENTIONAL FOOD |
|---|---|
| Calcium | Milk Products, Meat Products, Cheeses, Soybeans, Sardines, Salmon, Peanuts, Walnuts, Sunflower Seeds, Dried Beans, Kale, Broccoli, Collard Greens |

FIGURE 29

| INGREDIENT | CONVENTIONAL FOOD |
|---|---|
| Phosphorus | Fish, Poultry, Meat, Whole Grains, Eggs, Nuts, Seeds |

FIGURE 30

| INGREDIENT | CONVENTIONAL FOOD |
|---|---|
| Magnesium | Unmilled Grains, Figs, Almonds, Nuts, Seeds, dark-Green Vegetables, Bananas |

FIGURE 31

| INGREDIENT | CONVENTIONAL FOOD |
|---|---|
| Copper | Dried Beans, Peas, Whole Wheat, Prunes, Organ Meats, Shrimp, Seafood |

FIGURE 32

| INGREDIENT | CONVENTIONAL FOOD |
|---|---|
| Iodine | Kelp, Onions, Seafood |

FIGURE 33

| INGREDIENT | CONVENTIONAL FOOD |
|---|---|
| Iron | Pork liver, Beef Kidney, Beef Heart, Beef Liver, Farina, Raw Claims, Dried Peaches, Red Meat, Egg Yolks, Oysters, Nuts, Beans, Asparagus, Molasses, Oatmeal |

FIGURE 34

| INGREDIENT | CONVENTIONAL FOOD |
|---|---|
| Manganese | Whole-Grain Cereals, Nuts, Green Leafy Vegetables, Peas, Beets |

FIGURE 35

| INGREDIENT | CONVENTIONAL FOOD |
|---|---|
| Zinc | Meat, Liver, Seafood, Oysters, Wheat Germ, Brewer's Yeast, Pumpkin Seeds, Eggs, Nonfat Dry Milk, Ground Mustard |

NUTRITIONAL COMPOSITION MADE FROM CONVENTIONAL FOODS FOR MIXING ONSITE IN A BLENDER AND TREATING PATIENTS WITH HEPATIC DISORDERS

BACKGROUND OF THE INVENTION

1. Field of the Invention

The present invention relates to a nutritional composition. More particularly, the present invention relates to a nutritional composition made from conventional foods for mixing on site in a blender and treating patients with hepatic disorders.

2. Description of the Prior Art

The liver, and its proper functioning, is of utmost importance to the survival of a patient. Because it is responsible for the metabolism of nearly all nutrients, and is the primary site for the inactivation of numerous toxins, the liver is one of the most important organs of the body. For example, the liver accounts for approximately 20% of the body's basal metabolism.

The liver extracts a majority of the amino acids, carbohydrates, lipids, vitamins, and minerals from portal circulation. These nutrients, extracted by the liver, are used as substrates or cofactors in all metabolic processes carried out in the liver. Synthesis of plasma proteins and bile secretion are additionally important processes carried out by the liver.

Due to a variety of insults and pathogens, the liver can become diseased. Liver disease is a broad classification encompassing a number of acute and chronic diseases.

These diseases include hepatitis (viral and non-viral), cirrhosis (alcoholic and non-alcoholic), and liver failure. Liver failure is perhaps the most severe disease and may be accompanied by a complex set of conditions including hepatic encephalopathy, hemorrhage, coagulapathy, ascites, jaundice, and hepatorenal syndrome.

Although many medical treatments have been devised for treating liver disease, due to the paradoxical relationship between hepatic function and metabolism, medical treatment of the liver disease is complex and difficult. Most, if not all, liver diseases require or benefit from nutritional management. Those diseases which are believed to benefit most from nutritional management, include alcoholic and non-alcoholic cirrhosis, obstructive jaundice, and in some situations, acute liver failure. The goals of such nutritional therapies vary depending on disease and patient. The goals can be either restorative or supportive.

Liver disease can affect both hepatic cellular function and structure. In chronic conditions, such as alcoholic cirrhosis, exposure to a toxicant promotes inflammation of the periportal areas of the liver. As a result, fibrosis develops and when sufficiently advanced, canaliculi become blocked. As a result of inadequate regional perfusion, hepatocyte degeneration occurs.

In an attempt to restore adequate circulation, portal hypertension develops. Porto systemic shunting of the blood results in chronic hypertension. Many of the serious complications of liver disease are due to this event.

Porto systemic shunting allows many substances, for example, amino acids, fatty acids, ammonia, and others, to bypass the liver. These substances then flood the neurological system. Porto systemic shunting results in many clinical features including variceal changes and encephalopathy.

Many specific metabolic derangements are associated with liver disease. This is especially true of liver disease of a chronic nature. Such derangements include increased plasma glycogen, hyperinsulinemia, increased plasma epinephrine and cortisol, decreased liver and muscle carbohydrate stores, accelerated gluconeogenesis, hypoglycemia, hyperammonemia, increased plasma aromatic amino acid, increased plasma methionine, glutamine, asparagine, and histidine, and decreased plasma branched chain amino acids.

A number of hypotheses, mostly metabolism based, have been advanced to concerning the pathogenesis of hepatic encephalopathy. For example, excess nitrogen (ammonium) production and accumulation of false neural transmitters have been advanced as possible causes.

Numerous innovations for nutritional compositions have been provided in the prior art that will be described. Even though these innovations may be suitable for the specific individual purposes to which they address, however, they differ from the present invention in that they do not teach a nutritional composition made from conventional foods for mixing onsite in a blender and treating patients with hepatic disorders.

FOR EXAMPLE, U.S. Pat. No. 4,497,800 to Larson et al. teaches a nutritionally complete ready-to-use liquid diet for providing total patient nourishment. This diet contains a source of protein equivalent comprised of free amino acids and small peptides; a carbohydrate source comprised of maltodextrin with a dextrose equivalent between 7 and 24 and a smaller amount of modified corn starch; a lipid component; nutritionally significant amounts of all essential vitamins and minerals; and stabilizers; all in an acidic aqueous emulsion which can be sterilized.

ANOTHER EXAMPLE, U.S. Pat. No. 4,753,926 to Lucas et al. teaches infant foods suitable for use in the feeding of low birth weight infants, more especially preterm infants, are disclosed. The foods contain a relatively high level of vitamin $B_2$ and may be prepared so as to have an opacity greater than that of human breast milk leading to less susceptibility of the vitamin $B_2$ to breakdown by UV-light when used for the feeding of low birth weight infants who are receiving photo therapy. Preferred infant foods according to the invention also have high contents of vitamin $B_6$, vitamin C, vitamin D, vitamin E, folic acid, copper and zinc while containing no added iron. Another aspect of the invention is the inclusion of taurine and carnitine. One unexpected property of the infant foods according to the invention with high vitamin content is that their use has it been found to reduce the incidence of hyperbilirubinaemia in low birth weight infants.

STILL ANOTHER EXAMPLE, U.S. Pat. No. 5,413,803 to Chung teaches a nutritious milk composition containing a specific ratio of raw soybean milk to raw cows' milk which is an effective milk product for the regulation of micro nutrients, e.g., methionine and calcium contents and for the production of a synergistic effect between saturated and unsaturated fatty acids.

YET ANOTHER EXAMPLE, U.S. Pat. No. 5,728,678 to Trimbo et al. teaches a composition as well as method for providing nutrition to renal patients. Pursuant to the present invention, the enteral composition includes an effective amount of a protein source including whey protein and free amino acids that provide essential as well as nonessential amino acids. The composition is calorically dense and has a moderate osmolality.

It is apparent that numerous innovations for nutritional compositions have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a nutritional composition made from conventional foods for mixing onsite in a blender and treating patients with hepatic disorders that avoids the disadvantages of the prior art.

ANOTHER OBJECT of the present invention is to provide a nutritional composition made from conventional foods for mixing onsite in a blender and treating patients with hepatic disorders that is simple and inexpensive to manufacture.

STILL ANOTHER OBJECT of the present invention is to provide a nutritional composition foods for mixing onsite in a blender and treating patients with hepatic disorders that is simple to use.

BRIEFLY STATED, YET ANOTHER OBJECT of the present invention is to provide a nutritional composition made from conventional food for mixing on-site in a blender and treating patients with hepatic disorders. The composition includes a vitamin A enriched conventional food, a vitamin D enriched conventional food, a vitamin E enriched conventional food, a vitamin K enriched conventional food, a vitamin C enriched conventional food, a thiamine enriched conventional food, a riboflavin enriched conventional food, a niacin enriched conventional food, a pyridoxine enriched conventional food, a folic acid enriched conventional food, a pantothenic acid enriched conventional food, a vitamin B12 enriched conventional food, a biotin enriched conventional food, a chlorine enriched conventional food, a sodium enriched conventional food, a potassium enriched conventional food, a chlorine enriched conventional food, a calcium enriched conventional food, a phosphorus enriched conventional food, a magnesium enriched conventional food, a copper enriched conventional food, an Iodine enriched conventional food, a manganese enriched conventional food, and a zinc enriched conventional food.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The drawings are briefly described as follows:

FIG. 1 is a table of the ingredients for a 1000 ml example of the composition of the present invention having a density of 1125 g/liter and a pH of 6.8;

FIG. 2 is a table of the fat composition for a 1000 ml example of the composition of the present invention;

FIG. 3 is a table of the percentage composition of fat for the composition of the present invention FIG. 4 is a table of the composition of saturated fatty acids for the composition of the present invention;

FIG. 5 is a table of the composition of unsaturated fatty acids for the composition of the present invention;

FIG. 6 is a table of the composition of amino acids for the composition of the present invention;

FIG. 7 is a table of the major minerals in the composition of the present invention;

FIG. 8 is a table of the electrolyte ratios of the composition of the present invention;

FIG. 9 is a table of the protein composition of the composition of the present;

FIG. 10 is a table of the nitrogen to energy ratio of the composition of the present invention;

FIG. 11 is actable of the conventional foods containing the ingredient Vitamin A of the composition of the present invention;

FIG. 12 is a table of the conventional foods containing the ingredient Vitamin D of the composition of the present invention;

FIG. 13 is a table of the conventional foods containing the ingredient Vitamin E of the composition of the present invention;

FIG. 14 is a table of the conventional foods containing the ingredient Vitamin K of the composition of the present invention;

FIG. 15 is a table of the conventional foods containing the ingredient Vitamin C of the composition of the present invention;

FIG. 16 is a table of the conventional foods containing the ingredient Thiamine (B1) of the composition of the present invention;

FIG. 17 is a table of the conventional foods containing the ingredient Riboflavin (B2) of the composition of the present invention;

FIG. 18 is a table of the conventional foods containing the ingredient Niacin (PP) of the composition of the present invention;

FIG. 19 is a table of the conventional foods containing the ingredient Pyridoxine(B6) of the composition of the present invention;

FIG. 20 is a table of the conventional foods containing the ingredient Folic Acid of the composition of the present invention;

FIG. 21 is a table of the conventional foods containing the ingredient Pantothenic Acid of the composition of the present invention;

FIG. 22 is a table of the conventional foods containing the ingredient Vitamin B12 of the composition of the present invention;

FIG. 23 is a table of the conventional foods containing the ingredient Biotin of the composition of the present invention;

FIG. 24 is a table of the conventional foods containing the ingredient Choline of the composition of the present invention;

FIG. 25 is a table of the conventional foods containing the ingredient Sodium of the composition of the present invention;

FIG. 26 is a table of the conventional foods containing the ingredient Potassium of the composition of the present invention;

FIG. 27 is a table of the conventional foods containing the ingredient Chlorine of the composition of the present invention;

FIG. 28 is a table of the conventional foods containing the ingredient Calcium of the composition of the present invention;

FIG. 29 is a table of the conventional foods containing the ingredient Phosphorus of the composition of the present invention;

FIG. 30 is a table of the conventional foods containing the ingredient Magnesium of the composition of the present invention;

FIG. 31 is a table of the conventional foods containing the ingredient Copper of the composition of the present invention;

FIG. 32 is a table of the conventional foods containing the ingredient Iodine of the composition of the present invention;

FIG. 33 is a table of the conventional foods containing the ingredient Iron of the composition of the present invention;

FIG. 34 is a table of the conventional foods containing the ingredient Manganese of to the composition of the present invention; and FIG. 35 is a table of the conventional foods containing the ingredient Zinc of the composition of the present invention.

DETAILED DESCRIPTION OF THE PREFERRED EMBODIMENT

The present invention provides an enteral composition specifically designed for patients with hepatic disease. The composition is nutritionally complete, calorically dense, and suitable as a supplement or a total enteral feeding—either by tube or orally. The composition is specifically tailored to meet the requirements of hepatic patients in need of nutritional support.

In an embodiment, the nutritional composition made from conventional foods mixed onsite in a blender for treating patients with hepatic disorders of the present invention comprises:

1. Approximately 6% to 16% of the calories as a protein source.
2. Approximately 66% to about 88% of the calories as a carbohydrate source.
3. Approximately 6% to about 18% of the calories as a lipid source.

In a preferred embodiment, the composition comprises:
1. Approximately 11% of the calories as protein.
2. Approximately 77% of the calories as carbohydrate.
3. And approximately 12% as lipid.

The composition is specifically tailored to meet the needs of liver diseased patients. As set forth in the background of the invention, these patients suffer the possibility of a number of derangements.

Because of the liver's fundamental role in the metabolism of nearly all nutrients, hepatic disease can easily compromise nutritional status. Therefore, malnutrition is common in hepatic diseased patients. It has been estimated, with respect to alcoholic cirrhotics with severe liver disease, that 10% to 100% of such patients are malnourished. See, McCulloush et al., Nutritional State in Liver Disease Assessment, Incidence and Mechanism of Malnutrition, Metabolism and Nutrition in Liver Disease, E. Holm et al. (Editors) 1984, p. 5–15. This malnutrition develops as a result of a number of factors including anorexia, nutrient malabsorption and maldigestion, reduced food intake, and possibly increased energy expenditure.

Malabsorption also frequently occurs in patients with liver disease particularly in malnourished patients. Fat malabsorption is frequent. In one study, 8 out of 13 malnourished cirrhotics demonstrated fat malabsorption. Romiti et al., Malabsorption and Nutritional Abnormalities in Patients with Liver Disease, Ital. J. Gastroenterol., 1990; 22:118–123.

It is necessary for the hepatic composition of the present invention to provide adequate energy intake to support protein synthesis. If energy intakes are inadequate, amino acids will be used to support energy demands. Conversely, excess caloric intake will result in increased deposition of fat in the liver, which can result in further metabolic impairment of the liver. The composition of the present invention provides normal nutritional status and supports hepatocyte regeneration.

Although most stable cirrhotic patients have no overt problems digesting and absorbing protein and amino acids, investigators have reported derangements in such patient's plasma amino acid profiles. See, Morgan et al., Plasma Amino Acid Patterns In Liver Disease, Gut 1982; 23:362–370. This suggests altered tissue utilization of amino acids. For example, plasma levels of leucine, isoleucine, and valine concentrations in hepatic patients are low. Additionally, methionine and aromatic amino acids, i.e., tryptophan, tyrosine, and phenylalanine concentrations are elevated. The composition of the present invention is specifically tailored to correct these abnormalities.

The composition of the present invention provides 6% to 16% of the composition, by caloric content, as protein. In a preferred embodiment 11% of the composition, by caloric content, is provided as protein or 40 g of protein per liter (1500 kcals). Pursuant to the present invention, the protein comprises at least 25% and preferably 50% free crystalline amino acids. In a preferred embodiment, almost 75% of the protein is free crystalline amino acids. It has been found that by providing approximately 20%–40%, preferably 20%–25%, of the protein as whey or other protein, a free amino acid rich protein source that is sufficiently stable can be provided.

The protein is preferably provided as a mixture of specific essential and non-essential amino acids and whey protein. The amino acid profile is rich in branched chain amino acids, preferably approximately 40% to about 60%, and most preferably 50%, and low in ammonotelic amino acids (3%) in order to offset the amino acid derangements associated with hepatic disease. The total protein content is designed to meet the nutritional requirements, promote muscle anabolism, and minimize ammonia production, but limit intake in persons who are protein intolerant.

The use of enriched branched amino acids is advantageous especially with respect to treating hepatic encephalopathy. It is believed that branched chain amino acids can either improve recovery from or, in combination with other therapy, improve such treatment. Additionally, branched chain amino acids can decrease protein catabolism, increase synthesis of hepatic and muscle protein, and serve as energy substrates for muscle tissues. Ammonia production may also be reduced when branched chain amino acids are given as a substrate. Further, branched chain amino acids can improve nitrogen balance.

During bouts of encephalopathy, protein restrictions below that required to maintain body stores, is often prescribed (less than 0.8 grams protein per Kg per day). This, however, often results in negative nitrogen balance and additional loss of the lean body mass, ultimately contributing to further decline in nutritional and perhaps disease status. Accordingly, pursuant to the present invention, protein intake is carefully matched to the requirements to achieve optimal repletion with minimum negative clinical consequences. The amino acid profiles are customized to meet protein requirements and correct disease related changes in amino acid metabolism.

One of the principal metabolic defects in patients with liver disease is glucose intolerance. Elevations in glucagon, free fatty acids, and growth hormone are commonly observed in such patients and may serve to sustain high insulin levels and exacerbate glucose intolerance.

The composition of the present invention provides 66% to about 88% of the caloric content as carbohydrates. In a preferred embodiment, the composition provides 77% of the calories, or 290 grams of carbohydrates per liter (1500 kcals) are provided. In a preferred embodiment, the carbohydrates are provided in the form of maltodextrin and modified corn starch. These are easily digested and well absorbed.

Additionally, preferably, the composition is virtually lactose free. This eliminates the risk of the hepatic patients developing symptoms of lactose intolerance.

With respect to the lipid content, primary metabolic derangement of lipid metabolism in liver disease patient is lipid malabsorption. The cause of fat malabsorption may vary depending on the nature and severity of the liver disease. Non-alcoholic cirrhotics manifest normal gut histology while alcoholic cirrhotics show some evidence of jejunal damage. In both populations there is likely to be a reduction in bile salt synthesis, which also contributes to fat malabsorption.

In an embodiment, the composition of the present invention provides approximately 6% to about 18% of the calories as lipid. However, the composition could provide up to 25% of the calories as lipid. In a preferred embodiment, the composition provides 12% of the caloric content, or 21 g lipid per liter (1500 kcals), in the form of lipids. In a preferred embodiment, the lipid content comprises a blend of medium chain triglyceride oil and long chain fatty acids.

Preferably, the blend of medium chain triglycerides to long chain triglycerides is 1:1 to about 3:1. In a preferred embodiment, a 66:34% blend of medium chain triglyceride oil and long chain fatty acids is provided. Medium chain triglycerides are well absorbed and a readily oxidizable source of calories. The substitution of medium chain triglycerides for long chain fatty acids will alleviate steatorrhea in some patients. In a number of hepatic patients—believed to be at least 10%—steatorrhea is severe.

To provide essential fatty acids, in an embodiment, canola oil, milk fat, corn oil, and/or soy lecithin are provided. Linoleic and linolenic acid are provided preferably in a proportion of 3:1 to 5:1 and, most preferably, 4:1.

Hepatic patients have, typically, abnormalities of vitamin nutriture. However, assessment of vitamin and mineral status of hepatic patients is very difficult. Commonly used plasma measurements may be profoundly altered by portosystemic shunting and hepatocyte degeneration. Depressed synthesis of visceral proteins may also influence plasma concentrations of vitamins, therefore, it is difficult to accurately characterize in a hepatic patient the severity of vitamin and mineral deficiencies.

However, it is clear that in hepatic patients, widespread suboptimal vitamin nurture is common. In general, hepatic stores of riboflavin, nicotinamide, pantothenic acid, and Vitamins B6, B12, and A are often depleted. See, Leevy etal., Vitamin and Liver Injury, Am. J. Clin. Nutr. 1970; 23: 493–499. The absorption of all fat soluble vitamins is also adversely affected by hepatic diseased.

Vitamin A status is often impaired in liver disease with severity and type of the disease being significant determinants of its gravity. Fat malabsorption secondary to bile acid deficiency, may also contribute to the development of vitamin A deficiency.

Normally, Vitamin D3 is transported to hepatic tissue. In the liver, Vitamin D3 is converted to 25-hydroxy Vitamin D3. The active form of the vitamin (1, 25 dihydroxy Vitamin D3) is due to a hydroxylation step that occurs in the kidney. Liver disease impairs the export of 25 hydroxy Vitamin D3 from the liver. See, Hepner G. et al., Abnormal Vitamin D Metabolism in Patients With Cirrhosis, Am. J. Dig. Dis., 1976; 21:527–535. Even though hepatic patients have normal serum levels of Vitamin D, they may therefore have it o reduced tissue stores.

Likewise, vitamin E status may be compromised by hepatic disease. This is particularly true with patients with malabsorption and diminished bile secretion. Vitamin K status may also be compromised. This may be attributed to both malabsorption and cholestasis.

Water soluble vitamin nutriture may be similarly deranged particularly in the case of pyridoxine, thiamine, folate, riboflavin, and vitamin B12. Folate deficiency is the most common aberration in hepatic disease patients, especially alcoholic cirrhotics. Clinically, anemia can develop in 3 to 6 weeks as a result of subnormal folate intake.

Deficiency of vitamin B12 can also develop in chronic liver disease.

Mineral nutriture may also be abnormal in patients with liver disease. Liver enzymes require as cofactors a number of trace elements, i.e. zinc, copper, nickel, selenium, chromium, and cobalt. Cirrhosis can readily deplete liver stores of these minerals, particularly zinc and copper. Deficiencies or depletion may contribute to poor tissue repair and possibly neurological abnormalities.

Hyponatremia is relatively common in cirrhotic patients. This state develops in conjunction with an increase in the total body sodium pool which results in fluid retention.

Increased sodium retention appears to result from increase aldosterone production. It is necessary to restrict sodium intake to reduce ascites and edema.

Hypokalemia occurs frequently among cirrhotic patients. If not managed properly, hypokalemic alkalosis develops and hepatic encephalopathy may develop or worsen. Therefore, control of dietary intake of potassium relative to other minerals is vital.

Due to hepatic disease, calcium, phosphorus, and magnesium stores are also depleted. This depletion can be linked to a number of derangements, e.g., metabolic bone disease.

The present invention provides preferably in 1500 kcal (1000 mls) at least 100% U.S. RDA of all vitamins except vitamin C. Vitamin C is provided at at least 150% of the U.S. RDA to meet stress augmented needs in most patients.

Additionally the composition provides 100% of U.S. RDA of calcium, phosphorus, magnesium, copper, iodine, iron, and zinc in 1500 kcals (1000 millimeters). In a preferred embodiment manganese is provided in concentrations of approximately 4 milligrams per 1500 kcals. Additionally, the composition also-provides preferably approximately 400 mg Choline per 1500 kcals.

Additionally, approximately 80 milligrams sodium, 330 milligrams potassium, and 375 milligrams chloride are provided per 250 ml. These concentrations allow flexibility in electrolyte management.

Little is known about the specific taurine and carnitine status or requirements for patients with liver disease. Taurine stores have been found to be depressed in patients with malabsorption syndromes. Additionally, liver malfunction is known to impair taurine synthesis. Biosynthesis of carnitine may also be reduced when liver function is abnormal. Preferably, the composition of the present invention provides approximately 120 mg taurine and 120 mg carnitine per 1500 kcals.

The ingredients for a 1000 ml example of the composition of the present having a density of 1125 g/liter and a pH of 6.8 are presented in tabular form in FIG. 1.

The fat composition for a 1000 ml example of the composition of the present invention is presented in tabular form in FIG. 2.

The percentage composition of fat for the composition of the present invention is presented in tabular form in FIG. 3.

The composition of saturated fatty acids for the composition of the present invention are presented in tabular form in FIG. 4.

The composition of unsaturated fatty acids for the composition of the present invention are presented in tabular form in FIG. 5.

The composition of amino acids for the composition of the present invention are presented in tabular form in FIG. 6.

The major minerals in the composition of the present invention are presented in FIG. 7.

The electrolyte ratios of the composition of the present invention are presented in FIG. 8.

The protein composition of the composition of the present invention is presented in FIG. 9.

The nitrogen to energy ratio of the composition of the present invention is presented in FIG. 10.

A table of the conventional foods containing the ingredient Vitamin A of the composition of the present invention is presented in FIG. 11.

A table of the conventional foods containing the ingredient Vitamin D of the composition of the present invention is presented in FIG. 12.

A table of the conventional foods containing the ingredient Vitamin E of the composition of the present invention is presented in FIG. 13.

A table of the conventional foods containing the ingredient Vitamin K of the composition of the present invention is presented in FIG. 14.

A table of the conventional foods containing the ingredient Vitamin C of the composition of the present invention is presented in FIG. 15.

A table of the conventional foods containing the ingredient Thiamine (B1) of the composition of the present invention is presented in FIG. 16.

A table of the conventional foods containing the ingredient Riboflavin (B2) of the composition of the present invention is presented in FIG. 17.

A table of the conventional foods containing the ingredient Niacin (PP) of the composition of the present invention is presented in FIG. 18.

A table of the conventional foods containing the ingredient Pyridoxine(B6) of the composition of the present invention is presented in FIG. 19.

A table of the conventional foods containing the ingredient Folic Acid of the composition of the present invention is presented in FIG. 20.

A table of the conventional foods containing the ingredient Pantothenic Acid of the composition of the present invention is presented in FIG. 21.

A table of the conventional foods containing the ingredient Vitamin B12 of the composition of the present invention is presented in FIG. 22.

A table of the conventional foods containing the ingredient Biotin of the composition of the present invention is presented in FIG. 23.

A table of the conventional foods containing the ingredient Choline of the composition of the present invention is presented in FIG. 24.

A table of the conventional foods containing the ingredient Sodium of the composition of the present invention is presented in FIG. 25.

A table of the conventional foods containing the ingredient Potassium of the composition of the present invention is presented in FIG. 26.

A table of the conventional foods containing the ingredient Chlorine of the composition of the present invention is presented in FIG. 27.

A table of the conventional foods containing the ingredient Calcium of the composition of the present invention is presented in FIG. 28.

A table of the conventional foods containing the ingredient Phosphorus of the composition of the present invention is presented in FIG. 29.

A table of the conventional foods containing the ingredient Magnesium of the composition of the present invention is presented in FIG. 30.

A table of the conventional foods containing the ingredient Copper of the composition of the present invention is presented in FIG. 31.

A table of the conventional foods containing the ingredient Iodine of the composition of the present invention is presented in FIG. 32.

A table of the conventional foods containing the ingredient Iron of the composition of the present invention is presented in FIG. 33.

A table of the conventional foods containing the ingredient Manganese of the composition of the present invention is presented in FIG. 34.

A table of the conventional foods containing the ingredient Zinc of the composition of the present invention is presented in FIG. 35.

It will be understood that each of the elements described above, or two or more together, may also find a useful application in other types of constructions differing from the types described above.

While the invention has been illustrated and described as embodied in a nutritional composition made from conventional foods for mixing onsite in a blender and treating patients with hepatic disorders, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A nutritional composition made from conventional food for mixing on-site in a blender and treating patients with hepatic disorders, said composition comprising a blended mixture of:
    a) a vitamin A enriched conventional food;
    b) a vitamin D enriched conventional food;
    c) a vitamin E enriched conventional food;
    d) a vitamin K enriched conventional food;
    e) a vitamin C enriched conventional food;
    f) a thiamine enriched conventional food;
    g) a riboflavin enriched conventional food;
    h) a niacin enriched conventional food; and
    i) a chloine enriched conventional food wherein the composition is.

2. The composition as defined in claim 1, wherein said vitamin A enriched conventional food is selected from the group consisting of fish liver oil, liver, carrots, dark green vegetables, dark yellow vegetables, eggs, milk products, dairy products, margarine, and yellow fruits.

3. The composition as defined in claim 1, wherein said vitamin D enriched conventional food is selected from the group consisting of fish liver oils, sardines, herring, salmon, tuna, milk, and dairy products.

4. The composition as defined in claim 1, wherein said vitamin E enriched conventional food is selected from the group consisting of wheat germ, soybeans, vegetable oils, nuts, brussels sprouts, leafy green vegetables, spinach, enriched flour, whole wheat, whole-grain cereals, and eggs.

5. The composition as defined in claim 1, wherein said vitamin K enriched conventional food is selected from the group consisting of leafy green vegetables, yogurt, alfalfa, egg yolk, safflower oil, soybean oil, fish liver oils, and kelp.

6. The composition as defined in claim 1, wherein said vitamin C enriched conventional food is selected from the group consisting of citrus fruits, berries, green vegetables, leafy vegetables, tomatoes, cauliflower, potatoes, and peppers.

7. The composition as defined in claim 1, wherein said thiamine enriched conventional food is selected from the group consisting of brewer's yeast, rick husks, unrefined cereal grains, whole wheat, oatmeal, peanuts, organic meats, lean pork, vegetables, bran, and milk.

8. The composition as defined in claim 1, wherein said riboflavin enriched conventional food is selected from the group consisting of milk, liver, kidney, yeast, cheese, leafy green vegetables, fish, and eggs.

9. The composition as defined in claim 1, wherein said niacin enriched conventional food is selected from the group consisting of liver, lean meat, whole wheat products, brewer's yeast, kidney, wheat germ, fish, eggs, roasted peanuts, poultry white meat, avocados, dates, figs, and prunes.

10. The composition as defined in claim 1, wherein said composition further comprises:
    a) a pyridoxine enriched conventional food;
    b) a folic acid enriched conventional food;
    c) a pantothenic acid enriched conventional food;
    d) a vitamin B12 enriched conventional food;
    e) a biotin enriched conventional food;
    f) a sodium enriched conventional food; and
    g) a potassium enriched conventional food.

11. The composition as defined in claim 10, wherein said pyridoxine enriched conventional food is selected from the group consisting of brewer's yeast, wheat bran, wheat germ, liver, kidney, soy beans, cantaloupe, cabbage, blackstrap molasses, unmilled rice, eggs, oats, peanuts, and walnuts.

12. The composition as defined in claim 10, wherein said folic acid enriched conventional food is selected from the group consisting of deep-green leafy vegetables, carrots, tortula yeast, liver, egg yolk, cantaloupe, apricots, pumpkins, avocados, beans, whole rye flour, and dark rye flour.

13. The composition as defined in claim 10, wherein said pantothenic acid enriched conventional food is selected from the group consisting of meat, whole grains, wheat germ, bran, kidney, liver, heart, green vegetables, brewer's yeast, nuts, chicken, and crude molasses.

14. The composition as defined in claim 10, wherein said vitamin B12 enriched conventional food is selected from the group consisting of liver, beef, pork, eggs, milk, cheese, and kidney.

15. The composition as defined in claim 10, wherein said biotin enriched conventional food is selected from the group consisting of beef liver, egg yolk, soy flour, brewer's yeast, milk, kidney, and unpolished rice.

16. The composition as defined in claim 1, wherein said chlorine enriched conventional food is selected from the group consisting of egg yolks, brain, heart, green leafy vegetables, yeast, liver, and wheat germ.

17. The composition as defined in claim 10, wherein said sodium enriched conventional food is selected from the group consisting of salt, shellfish, carrots, beets, artichokes, dried beef, brains, kidney, and bacon.

18. The composition as defined in claim 10, wherein said potassium enriched conventional food is selected from the group consisting of citrus fruits, cantaloupe, tomatoes, watercress, green leafy vegetables, mint leaves, sunflower seeds, bananas, and potatoes.

19. The composition as defined in claim 1, wherein said composition further comprises:
    a) a chlorine enriched conventional food;
    b) a calcium enriched conventional food;
    c) a phosphorus enriched conventional food;
    d) a magnesium enriched conventional food;
    e) a copper enriched conventional food;
    f) an Iodine enriched conventional food;
    g) a manganese enriched conventional food; and
    h) a zinc enriched conventional food.

20. The composition as defined in claim 19, wherein:
    a) said chlorine enriched conventional food is selected from the group consisting of table salt, kelp, and olives;
    b) said calcium enriched conventional food is selected from the group consisting of milk products, meat products, cheeses, soybeans, sardines, salmon, peanuts, walnuts, sunflower seeds, dried beans, kale, broccoli, and collard greens;
    c) said phosphorus enriched conventional food is selected from the group consisting of fish, poultry, meat, whole grains, eggs, nuts, and seeds;
    d) said magnesium enriched conventional food is selected from the group consisting of unmilled grains, figs, almonds, nuts, seeds, dark-green vegetables, and bananas;
    e) said copper enriched conventional food is selected from the group consisting of dried beans, peas, whole wheat, prunes, organ meats, shrimp, and seafood;
    f) said iodine enriched conventional food is selected from the group consisting of kelp, onions, seafood, iron, pork liver, beef kidney, beef heart, beef liver, farina, raw claims, dried peaches, red meat, egg yolks, oysters, nuts, beans, asparagus, molasses, and oatmeal;
    g) said manganese enriched conventional food is selected from the group consisting of whole-grain cereals, nuts, green leafy vegetables, peas, and beets; and
    h) said zinc enriched conventional food is selected from the group consisting of meat, liver, seafood, oysters, wheat germ, brewer's yeast, pumpkin seeds, eggs, nonfat dry milk, and ground mustard.

* * * * *